United States Patent [19]
Breinholt et al.

[11] Patent Number: 5,631,223
[45] Date of Patent: May 20, 1997

[54] FUNGICIDALLY ACTIVE COMPOUNDS

[75] Inventors: Jens Breinholt, Bagsvaerd; Ruby I. Nielsen, Farum; Georg W. Jensen, Bagsvaerd, all of Denmark

[73] Assignee: Novo Nordisk A/S, Bagsvaerd, Denmark

[21] Appl. No.: 468,157

[22] Filed: Jun. 6, 1995

Related U.S. Application Data

[62] Division of Ser. No. 984,563, filed as PCT/DK91/00273 Sep. 17, 1991, Pat. No. 5,514,648.

[30] Foreign Application Priority Data

Sep. 17, 1990 [DK] Denmark ................ 2236/90

[51] Int. Cl.$^6$ ................ C07K 11/02; C12P 21/04; C12N 1/14; A01N 63/04
[52] U.S. Cl. ................ 514/9; 435/71.1; 435/254.1; 530/321
[58] Field of Search ................ 435/71.1, 254.1; 530/321; 514/9

[56] References Cited

U.S. PATENT DOCUMENTS 4,776,873  10/1988  Caulder et al. ................ 71/79

FOREIGN PATENT DOCUMENTS 0207653  1/1987  European Pat. Off. .
0360760  3/1990  European Pat. Off. .

OTHER PUBLICATIONS

Marci et al., Physiol. Plant Path., vol. 8, pp. 325–331 (1976).
Olufolaji, Cryptogamie Mycol. vol. 7. (4), pp. 335–342 (1986).
Coombe et al., Aust. J. Chem., vol. 21, pp. 783–788 (1968).
O.C. Musgrave, J. Schem. Soc., pp. 4301–4304 (1956).

*Primary Examiner*—Herbert J. Lilling
*Attorney, Agent, or Firm*—Steve T. Zelson, Esq.; Cheryl H. Agris, Esq.

[57] ABSTRACT

Novel compounds of the general composition I, Lactate (1), Glycine (1), Valine (1), Isoleucine (1), pipecolic acid (1), Aspanic acid (1), Tyrosine (1), wherein each amino acid residue independently may occur in L- or D- form, and wherein the number in parenthesis indicates the number of occurrences of each moiety, and derivatives thereof are disclosed. The compounds are producible by aerobic cultivation on suitable nutrient media under suitable conditions of a strain of the fungus Culvularia sp., subsequent recovery of the active component from the fermentation medium, and optionally modifying the active compound to obtain a compound of the desired general composition. Disclosed are also microorganisms capable of producing said compounds, compositions containing said compounds, and the use of such compositions for controlling fungi in crops, and in the preservation of wood, paints, cosmetics, and edible products.

10 Claims, 10 Drawing Sheets

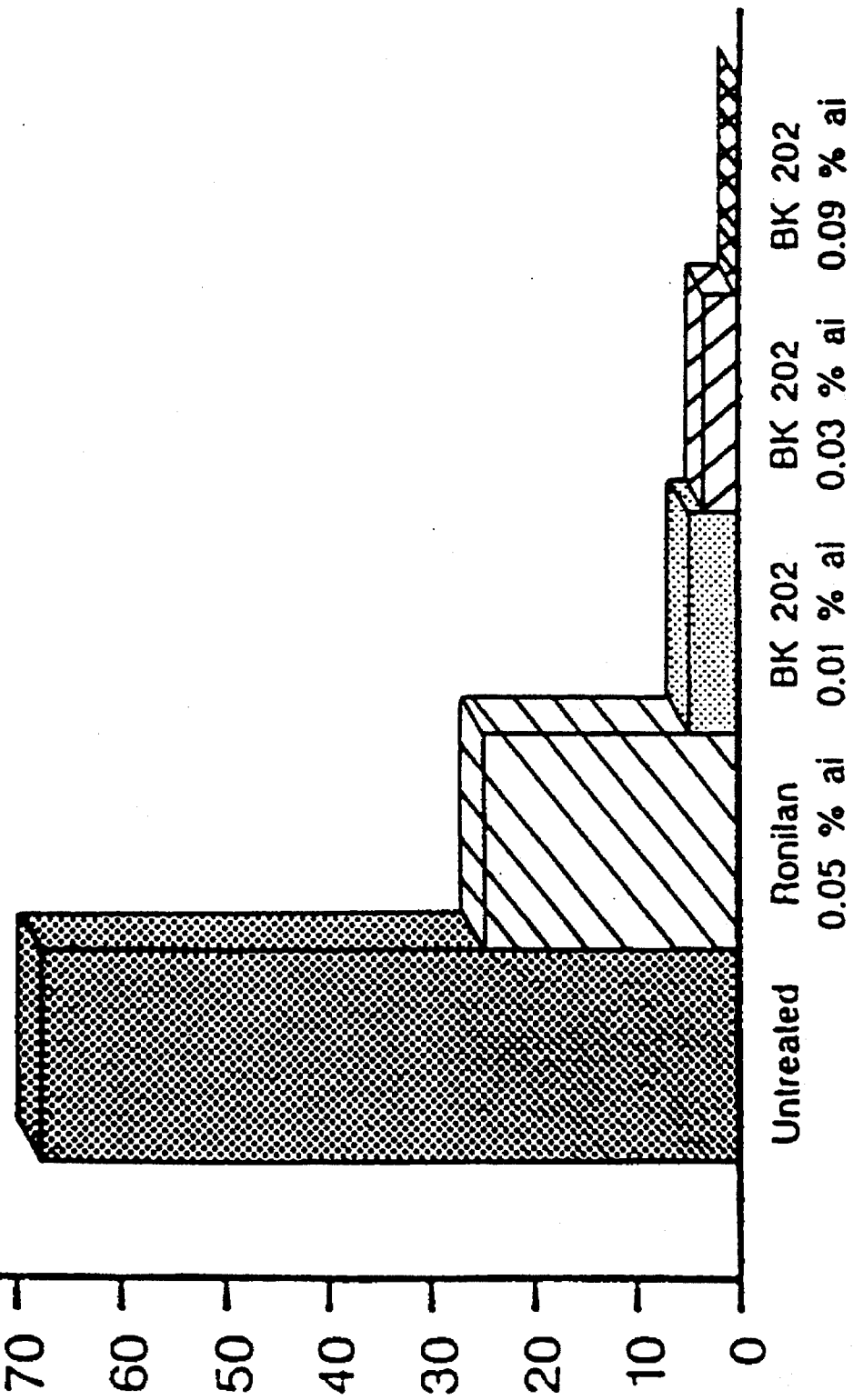

FUNGICIDALLY ACTIVE COMPOUNDS

This is a divisional application of application Ser. No. 07/984,563, filed Aug. 16, 1993 the contents of which are incorporated herein by reference in their entirety, now U.S. Pat No. 5,514,648, which is a national stage application filed under 35 USC 371 of PCT/DIC91/00273 filed Sep. 17,1991.

FIELD OF THE INVENTION

This invention relates to novel fungicidally active compounds, methods of producing such compounds, microorganisms capable of producing said compounds, compositions containing said compounds, and the use of such compositions for controlling fungi in valuable crops, animals, including birds and mammals, and in the preservation of wood and timber, paints, cosmetics, foods and feeds.

BACKGROUND OF THE INVENTION

For a number of years it has been known that various microorganisms produce metabolites exhibiting biological activity so as to be useful as biocides for combating diseases and pests.

Especially it has been known that some species of the genus Curvularia produce different metabolites exhibiting biological activity, in particular as phytotoxins. However, none of these metabolites are known to be fungicides. *C. lunata* (Wakk.) Boed was found to produce at least two phytotoxins. They cause necrotic spots on plant leaves even when they are highly diluted. (F. Macrí and A. Viahello, *Physiological Plant Pathology* 8:325–331, 1976). The toxins are phytotoxins and are non host specific. Host specific toxins have been isolated from culture filtrates of *C. pallescens* Boedijn and from diseased host leaves attacked by this species (Olufolaji, *Crytogamie Mycol.* 7(4):335–342, 1986). These toxic substances gave chlorotic spots to maize plants. They later became necrotic similar to in-vivo symptoms of the disease caused by *C. pallescens*.

Curvularin, a macrocyclic metabolite, has been isolated from a Curvularia species (O. C. Musgrave, *J. Chem Soc.*, 1956, 4301) and from *C. lunata* (Coombe et al, *Aust. J. Chem.* 21:783, 1968). The compound has the formula $C_{16}H_{20}O_5$ (molecular weight 292.3) and has the formula 1 below:

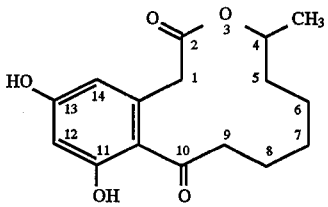

Crude curvularin was isolated as colourless or pale yellow-brown crystals.

Neither curvularin nor the crude filtrates from Curvularia showed anti-bacterial activity (against *Bacillus subtilis, Escerichia coli,* and *Staphylococcus aureus*) or anti-fungal activity (spore germination test with *Penicillium digitatum*).

None of the above compounds are useful for combating plant diseases and pests because they are strong phytotoxins.

Although progress has been made in the field of identifying and developing biological biocides for combating various diseases and pests in plants and animals of agronomical importance, most of the biocides in use are still synthetic compounds that are difficult to decompose in nature and have a broad spectrum of activity.

In the last decade or so there has been a still increasing concern for the impact of such biocides on the environment and the ecosystems surrounding farmlands and consequently there exists an outspoken need for biocides that are more specific in their activity, and are readily degradable in the natural environment.

A number of compounds related to the compounds disclosed through this invention have been disclosed in European Publication No. EP 360 760 (Sandoz AG), published 28.3.1990. These compounds are disclosed as being produced by the fungal genus Septoria, and as having interesting pharmacological properties, e.g. antifungal activity in animals against yeast and yeast-like species causing systemic attacks. The publication contains only reference to one test against Candida, and no reference to which of the 82 exemplified compounds were tested for this activity, but states that the most preferred compound can be represented by the formula:

cyclo-[Pec-MeVal-Val-MeAsp-MeIle-MeIle-Gly-MeVal-TyrOMe-D-Lact]           (Example 1, first compound).

SUMMARY OF THE INVENTION

As indicated above known metabolites from the mold genus Curvularia all have exhibited a strong phytotoxic activity, but it has now surprisingly been found that fungi belonging to said genus also produce metabolites that exhibit strong antifungal activity, and that are substantially without phytotoxic activity.

The present invention in its first aspect concerns a group of novel compounds comprising compounds having the general composition I, Lactate (1), Glycine (1), Valine (4), Isoleucine (1), pipecolic acid (1), Aspartic acid (1), Tyrosine (1)           (I)

wherein each amino acid residue independently may occur in L- or D-form, and wherein the number in parenthesis indicates the number of occurrences of each moiety, and derivatives thereof.

Under this aspect the invention also relates to compounds of the composition $C_{56}H_{89}N_9O_{14}$ and derivatives thereof.

In a specific aspect the invention relates to such compounds of the general composition II Lactate (1), Glycine (1), Valine (1), N-Me-Valine (3), N-Me-Isoleucine (1), pipecolic acid (1, N-Me-Aspartic acid (1), O-Me-Tyrosine (1),           (II)

wherein each amino acid residue independently may occur in L- or D-form, and, wherein the number in parenthesis indicates the number of occurrences of each moiety, and derivatives thereof.

In a specific aspect the invention relates to the compounds of formulae III and IV

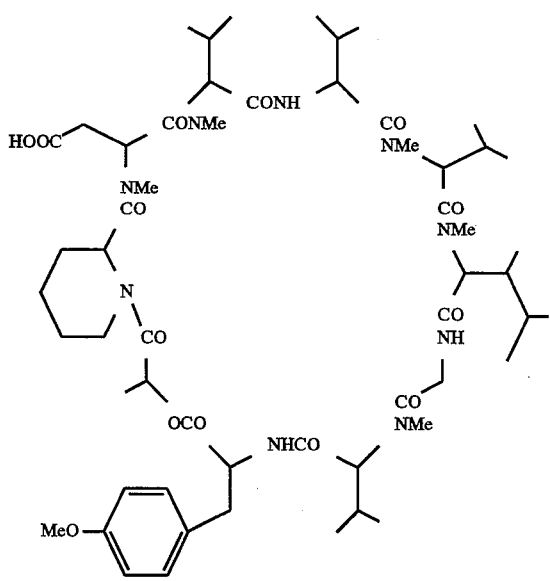

cyclo-[Pec-MeAsp-MeVal-Val-MeVal-MeIle-Gly-MeVal-TyrOMe-D-Lact]    (III)

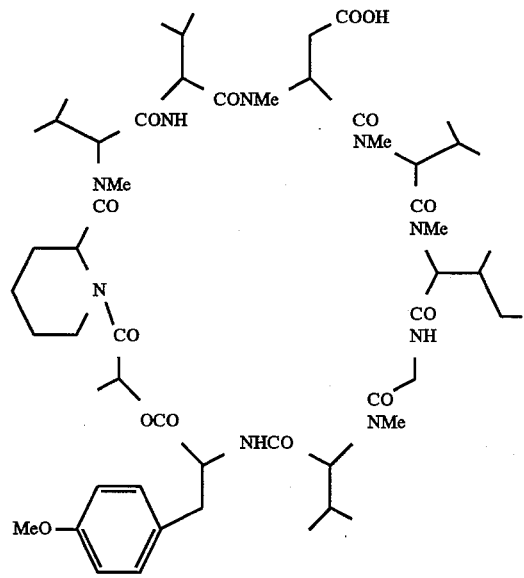

cyclo-[Pec-MeVal-Val-MeAsp-MeVal-MeIle-Gly-MeVal-TyrOMe-D-Lact]    (IV), wherein each amino acid residue and the lactate residue independently may occur in L- or D-form, and derivatives thereof. Most preferred are the compounds wherein all the amino acid residues are in the L-form and the lactate residue is in the D-form.

In its second aspect the invention relates to processes used for the production of the novel compounds of the invention. These processes comprise use of specific microorganisms as well as chemical processes for full or semi synthetic production of said compounds.

In a third aspect of the invention it relates to fungicidal compositions comprising the novel compounds of the invention in combination with suitable excipients, such as diluents, carriers, etc.

The invention also relates to the use of microorganisms producing the compounds of the invention as fungicidal compositions.

Within the context of the invention it is also contemplated to combine the novel compounds of the invention with known biocides for making up novel combination compositions.

Furthermore the invention in a fourth aspect relates to methods of combating plant diseases by application of compositions comprising the novel compounds of the invention to infested areas.

In a fifth aspect the invention relates to the use of the novel compounds of the invention for combating or controlling plant diseases, especially fungal attack.

Also the invention relates to the use of the novel compounds as preservatives and/or additives to control fungi in foods and feeds, timber and wood, paints, growth media, cosmetics, etc.

Lastly the invention relates to an isolated pure culture of the microorganism Curvularia sp. (CMI CC No. 337159).

DEPOSITION OF MICROORGANISM

For the purpose of describing this invention in detail a strain of the fungus Curvularia sp. (CMI CC No. 337159) has been deposited with the Commonwealth Mycological Institute Culture Collection (CMI CC), Ferry Lane, Kew, Surrey TW9 3AF, England, for the purposes of patent procedure on the date indicated below. CMI CC being an international depository under the Budapest Treaty affords permanence of the deposit in accordance with rule 9 of said treaty.

| Deposit date | 6 February 1990 |
|---|---|
| Depositor's ref. | 33 177 |
| CMI CC designation | CMI CC No. 337159 |

CMI CC 337159 belongs to the class Deuteromycetes, sub-class Hyphomycetidae and family Dematiaceae. The fungus is a new species of the genus Curvularia.

BRIEF DESCRIPTION OF THE DRAWING

The invention is described in further detail below with reference to the drawings, wherein

FIGS. 8, 9, and 10 show the results of applying a compound of the invention to Botrytis cinerea infected strawberries, grapes, and tomatoes, respectively.

DETAILED DESCRIPTION OF THE INVENTION

Figure 1:
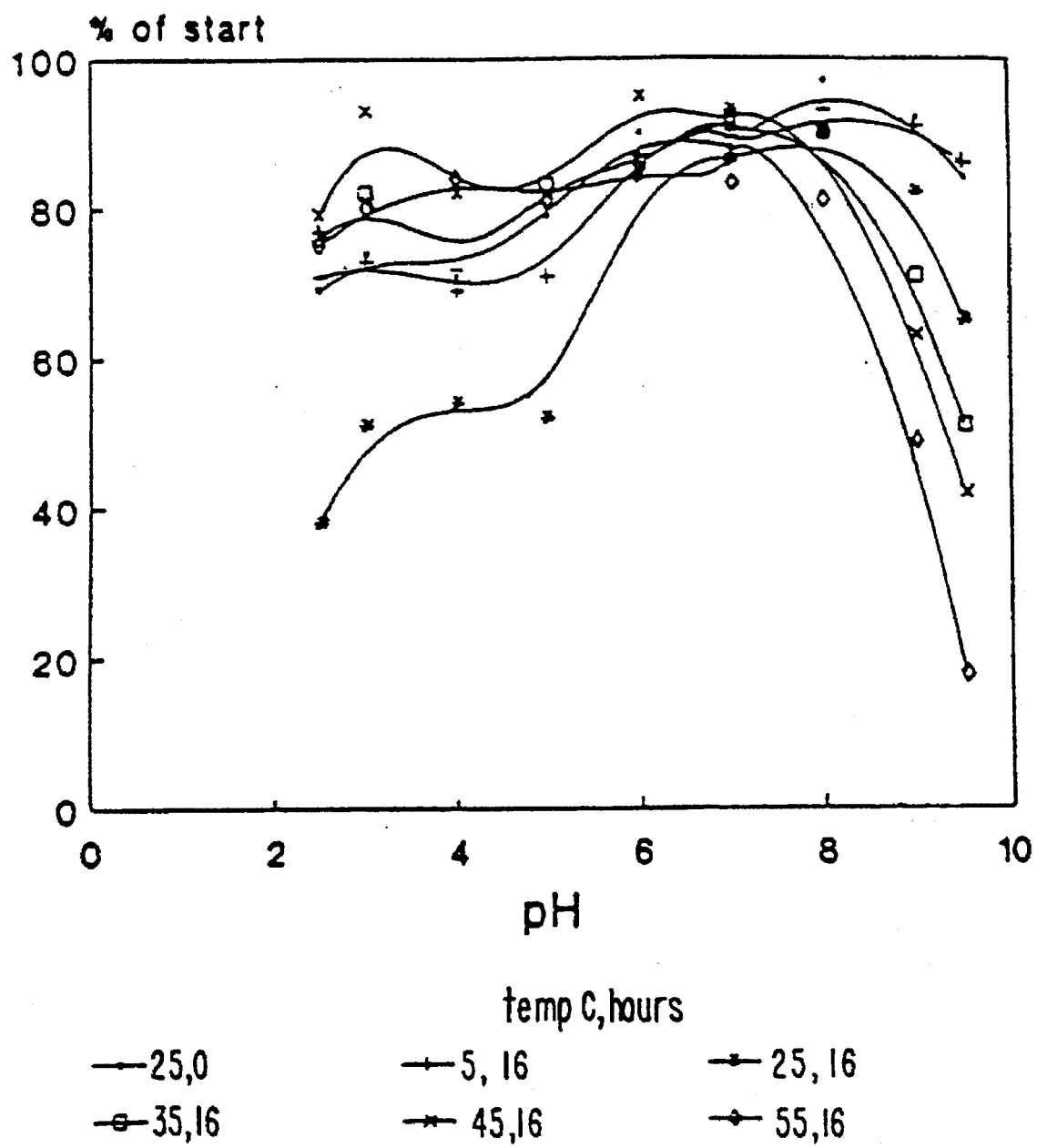
FIG. 1 shows a graphical representation of the stability/activity relationship with temperature and pH for a novel compound according to the invention.

As indicated above the invention relates in its first aspect to novel compounds of the general composition I, Lactate (1), Glycine (1), Valine (4), Isoleucine (1), pipecolic acid (1), Aspartic acid (1), Tyrosine (1)    (I)

wherein each amino acid residue independently may occur in L- or D-form, and wherein the number in parenthesis indicates the number of occurrences of each moiety, and derivatives thereof.

Within this aspect the invention furthermore comprises such compounds further comprising a lactone ring; and derivatives thereof.

The invention moreover comprises such compounds having the composition $C_{56}H_{89}N_9O_{14}$ and derivatives thereof.

Within this aspect the derivatives referred to above particularly comprise such compounds having been alkylated, hydroxylated, glycosylated, halogenated, reduced, oxidized, hydrolysed, or esterified.

In a specific aspect the invention relates to such compounds of the general composition II Lactate (1), Glycine (1), Valine (1), N-Me-Valine (3), N-Me-Isoleucine (1), pipecolic acid (1), N-Me-Aspartic acid (1), O-Me-Tyrosine (1),    (II)

wherein each amino acid residue independently may occur in L- or D-form, and, wherein the number in parenthesis indicates the number of occurrences of each moiety, and derivatives thereof.

As a specific example the invention relates to the compounds of formulae III and IV

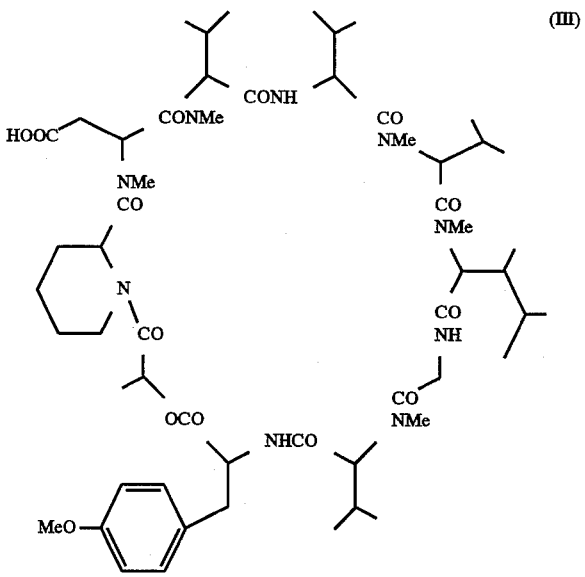

cyclo-[Pec-MeAsp-MeVal-Val-MeVal-MeIle-Gly-MeVal-TyrOMe-D-Lact]    (III)

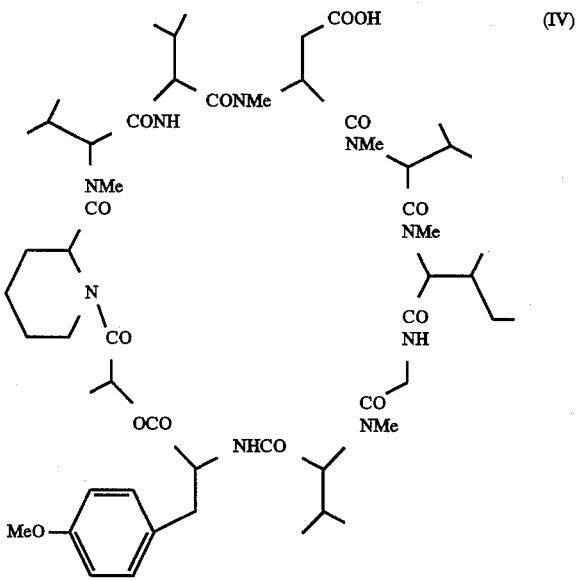

cyclo-[Pec-MeVal-Val-MeAsp-MeVal-MeIle-Gly-MeVal-TyrOMe-D-Lact]    (IV), wherein each amino acid residue and the lactate residue independently may occur in L- or D-form, and derivatives thereof. Most preferred are the compounds wherein all the amino acid residues are in the L-form and the lactate residue is in the D-form.

The compounds of formulae III and IV were isolated as metabolites from a novel species of the genus Curvularia, Curvularia sp. (CMI CC No. 337159).

Compounds of this class of organic structures with the formulae III and IV are novel. The closest reference is EP 360 760 discussed above. The compounds of EP 360 760 have as the main difference from those of the present invention that they always comprise two neighbouring isoleucine residues.

Although compunds closely related to the compounds of this invention are disclosed in EP 360760, the compounds there would not be considered for agronomical use. This is due to the high toxicity (approximately 100 mg/kg p.o.) and low antifungal activity (dosage 25 to 300 mg/kg, daily dosage of 300 to 3000 mg) as exemplified towards Candida on pages 47 to 49 of EP 360 760.

Furthermore EP 360 760 only indicates pharmaceutical usage of the related compounds. Consequently the surprising specificity and activity for the agronomical use of the compounds of the present invention can in no way be inferred from EP 360 760. According to its second aspect the invention relates to processes for the production of the novel compounds of the composition I.

The compounds of formulae III or IV may be prepared by aerobic cultivation on suitable nutrient media under conditions hereinafter described with a strain of a fungus belonging to the genus Curvularia, especially the fungus Curvularia sp. (CMI CC 337159), and thereafter recovering the active component from the biomass and from the fermentation medium.

The natural metabolite may subsequently be modified chemically in order to obtain various derivatives thereof. The derivatives may be produced in order to improve certain properties with the metabolite such as its solubility in aqueous media, its hydrophobicity, hydrophilicity, stability, specificity, etc.

It is also contemplated that compounds according to the invention may be produced by well known chemical synthetic processes using available starting materials.

Derivatives of related compounds and methods for producing such derivatives hereto are disclosed in detail in EP 360 760, which is hereby incorporated by reference.

A specific type of derivatives from the compounds of formulae III and IV are such compounds wherein the lactone ring has been opened.

One group of derivatives is compounds of composition I, II, III or IV, wherein one or several hydroxy and/or amino groups have been glycosylated with one or more sugar moieties.

Another group comprises compounds of composition I, II, III or IV, wherein one or several hydroxy and/or amino groups have been acylated with organic acids into ester/amide groups.

A further group of derivatives is compounds of composition I, II, III, or IV, wherein one or several hydroxy and/or amino groups have been alkylated into alkyl ethers/amines.

A further group of derivatives is compounds of composition I, II, III, or IV, wherein one or several groups have been substituted by halogenation into compounds, wherein one or more groups are halogens.

A further group of derivatives is compounds of composition I, II, III, or IV, wherein one or several groups have been altered by reduction of one or more groups in the compound obtained.

A further group of derivatives is compounds of composition I, II, III, or IV, wherein one or several groups have been altered by oxidation of one or more groups in the compound obtained.

A further group of derivatives is compounds of composition I, II, III, or IV, wherein one or several groups have been altered by hydrolysis of one or more groups in the compound obtained.

Although the invention discussed herein below, principally deals with the specific strain CMI CC 337159, it is well known in the art that the properties of microorganisms may be varied naturally and artificially. Thus all strains belonging to the genus Curvularia including variants, recombinants and mutants, whether obtained by natural selection, produced by the action of mutating agents such as ionizing radiation or ultraviolet irradiation, or by the action of chemical mutagens such as nitrosoguanidine, are included in this invention.

It is well known that a fungus is able to produce closely related metabolites (cf. EP 360 760, where three related compounds were produced by the same fungus) of the same or similar activity, but with minor differences in chemical structure. The present invention is therefore meant also to encompass such closely related compounds produced by CMI CC 337159.

Depending on the circumstances such as the crop wherein fungi are to be combated, the environmental conditions or other factors, a composition of the invention in addition to said fungicidally active compounds of the invention may also contain other active ingredients such as other biocides, such as fungicides, herbicides, insecticides, nematicides, acaricides, or plant nutrients, plant growth regulators, or fertilizers.

Examples of other fungicides which can be combined with the active compounds of the invention include especially ergosterol biosynthesis inhibitors ("EBIs"). These are generally imidazole or triazole derivatives and examples include those known by the common names prochloraz, triadimefon, propiconazole, diclobutrazol, triadiminol, flusilazole, flutriafol, myclobutanil, penconazole, quinconazole, imazalil and diniconazole. Examples of non azole EBIs include nuarimol, fenarimol, fenpropimorph, tridemorph and fenpropidine. Other fungicides which can be combined with the enzyme preparation of the invention include anilides, e.g. carboxin, metalaxyl, furalaxyl, ofurace; benalaxyl, mepronil, flutolanil, pencycuron and oxadixyl; benzimidazoles, e.g. benomyl and carbendazim; carbamates, e.g. maneb, mancozeb and propamocarb; dicarboximides, e.g. iprodione, vinclozolin and procymidone; phosphorus derivatives, e.g. pyrazophos, tolclofos-methyl and fosetyl aluminum; and miscellaneous compounds, including dithiocarbamates, bisdithiocarbamates, imidazoles, triazoles, phathalonitriles, polyhalogenalkylthio compounds, iminoctadine, guazatine, dicloran, chlorothalonil, pyrifexox, ethirimol, cymoxanil, phenyl pyrroles, thiocyofenes, pyrimidines, and anilazine.

For combating fungi in animals including humans the composition of the invention would usually comprise said active compounds of the invention alone with a physiologically compatible carrier or diluent, but it may also be combined with other active ingredients such as an antibioticum.

A fungicidal composition according to the invention having a fungicidally active compound of the invention as its active ingredient may for agronomical and/or horticultural applications be formulated by mixing the active principle with suitable inert and compatible carriers or diluents to obtain a composition of the type generally used in agricultural compositions such as a wettable powder, an emulsifiable concentrate, a concentrated emulsion, a granular formulation, a water soluble powder, an alginate, a xanthan gum and/or an aerosol. As solid carriers bentonite, diatomaceous earth, apatite, gypsum, talc, pyrophyllite, vermiculite, ground shells, and clay may be mentioned. A surface active agent may also be added with the purpose of producing a homogeneous and stable formulation.

The diluent or carrier in the composition of the invention can as indicated be a solid or a liquid optionally in association with a surface-active agent, for example a dispersing agent, emulsifying agent or wetting agent. Suitable surface-active agents include anionic compounds such as a carboxylate, for example a metal carboxylate of a long chain fatty acid; an N-acylsarcosinate; mono- or di-esters of phosphoric acid with fatty alcohol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl aryl sulphonates such as alkyl-benzene sulphonates or lower alkylnaphthalene sulphonates, e.g. butyl-naphthalene sulphonate; salts of sulphonated naphthalene-formaldehyde condensates; salts of sulphonated phenol-formaldehyde condensates; or more complex sulphonates such as the amide sulphonates, e.g. the sulphonated condensation product of oleic acid and N-methyl taurine or the dialkyl sulphosuccinates, e.g. the sodium sulphonate of dioctyl succinate. Non-ionic agents include condensation products of fatty acid esters, fatty alcohols, fatty acid amides or fatty-alkyl- of alkenyl-substituted phenols with ethylene oxide, fatty esters of polyhydric alcohol ethers, e.g. sorbitan fatty acid esters, condensation products of such esters with ethylene oxide, e.g. polyoxyethylene sorbitan fatty acid esters, block copolymers of ethylene oxide and propylene oxide, acetylenic glycols such as 2,4,7,9-tetraethyl-5-decyn-4,7-diol, or ethoxylated acetylenic glycols.

Examples of a cationic surface-active agent include, for instance, an aliphatic mo-no-, di-, or polyamine as an acetate, naphthenate or oleate; an oxygen-containing amine such as an amine oxide or polyoxyethylene alkylamine; an amide-linked amine prepared by the condensation of a carboxylic acid with a di- or polyamine; or a quaternary ammonium salt.

The compositions of the invention can take any form known in the art for the formulation of agrochemicals, for example, a solution, a dispersion, an aqueous emulsion, a dusting powder, a seed dressing, a dispersible powder, an emulsifiable concentrate or granules. Moreover, it can be in a suitable form for direct application or as a concentrate or primary composition which requires dilution with a suitable quantity of water or other diluent before application.

An emulsifiable concentrate comprises the active ingredient dissolved in a water-immiscible solvent which is formed into an emulsion with water in the presence of an emulsifying agent.

A dusting powder comprises the active ingredient intimately mixed and ground with a solid pulverulent diluent, for example, kaolin.

A granular solid comprises the active ingredient associated with similar diluents to those which may be employed in dusting powders, but the mixture is granulated by known methods. Alternatively it comprises the active ingredient absorbed or adsorbed on a pre-granular diluent for example, Fuller's earth, attapulgite or limestone grit.

Wettable powders, granules or grains usually comprise the active ingredient in admixture with a suitable surfactant and an inert powder diluent such as china clay.

Another suitable concentrate is a flowable suspension concentrate which is formed by grinding the active ingredient with water or other liquid, a wetting agent and suspending agent.

It is contemplated that the active compound of the invention may be applied in concentrations ranging from about 0.001 µg/ml to 750 mg/ml, preferably from 1 µg/ml to 10 mg/ml, for use in controlling fungi in plants.

For use in combating fungi in animals including mammals the active compounds of the invention may be formulated by mixing a compound of the invention with suitable inert and compatible carriers known in the art for use in topical formulations, or for use as a systemic agent, as applicable.

The concentration of the active compounds of the invention described herein in the compositions of the invention may vary within a wide range depending on the type of formulation and the field of application.

It is contemplated that the active compound of the invention may be applied in concentrations ranging from about 0.001 µg/ml to 10 mg/ml, preferably from 0.1 µg/ml to 1 mg/ml, for use in controlling fungi in animals.

In its fourth aspect the invention relates to methods of combating fungi in plants or animals including mammals, wherein an effective amount of a fungicidally active compound of the invention is applied to a region to be treated.

In connection with this aspect the compositions of the invention may for agronomical or horticultural uses be applied to a region to be treated either directly to the soil as a pro-emergence treatment to the seed surface as a seed dressing or to the foliage or fruits of the plants as a post-emergence treatment. Depending on the crop and circumstances the treatment may be postponed until seeds or fruits appear on the plants, wherein fungi are to be controlled.

The active preparation or the compositions of the invention can be applied directly to the plant by, for example, spraying or dusting either at the time when the fungus has begun to appear on the plant or before the appearance of fungus as a protective measure. In both such cases the preferred mode of application is by foliar spraying. It is generally important to obtain good control of fungi in the early stages of plant growth as this is the time when the plant can be most severely damaged. The spray or dust can conveniently contain a pre- or post-emergence herbicide, a mixture of other pesticides, plant growth regulators or fertilizers, if this is thought necessary.

Sometimes, it is practicable to treat the roots of a plant before or during planting, for example by dipping the roots in a suitable liquid or solid composition. When the active preparation of the invention is applied directly to the plant a suitable rate of application is from 0.001 to 50 kg per hectare, preferably from 0.05 to 5 kg per hectare.

In the method of the invention the active preparation of the invention alone or in combination with a conventional biocide can also be applied to seeds or habitat. Thus the preparation can be applied directly to the soil before, at or after drilling so that the presence of active ingredient in the soil can control the growth of fungi which may attack seeds.

The compositions may be applied in amounts corresponding to from about 1 g to about 100 kg fungicidally active compound per hectare.

When the soil is treated directly the active preparation (alone or in admixture with the conventional biocide) can be applied in any manner which allows it to be intimately mixed with the soil such as by spraying, by broadcasting a solid form of granules, or by applying the active ingredient at the same time as drilling by inserting it in the same drill as the seeds. A suitable application rate is within the range of from 0.01 to 50 kg per hectare, more preferably from 0.05 to 5 kg per hectare.

The concentration of the fungicidally active compounds of the invention in the compositions of the present invention when used alone or in combination with a conventional fungicide, as applied to plants is preferably within the range from about 0.001 to about 30 per cent by weight, especially 0.01 to 3.0 per cent by weight. In a primary composition the amount of active compound can vary widely and can be, for example, in the range from about 5 to about 95 per cent by weight of the composition.

The concentration of the other fungicidally active ingredient in the mixed composition of the present invention, as applied to plants is preferably within the range of 0.001 to 50 per cent by weight, especially 0.01 to 10 per cent by weight. In a primary composition the amount of other active ingredient can vary widely and can be, for example, from 5 to 80 per cent by weight of the composition.

Although the present invention has been described in detail in connection with controlling fungi in animals and plants, it is also anticipated that the fungicidally active compounds of the invention may be used for the preservation of wood by adding said compounds to wood preservation and/or impregnation compositions. Also, the active compounds of the invention may be useful as a fungicide and preservant in paints—both to prevent growth in the paint during storage, and growth on the painted object such as the plastered surface of a house.

Further the fungicidally active compounds of the invention may due to their low toxicity be used for the preservation of cosmetics, foods and feeds, or other such items where the compounds may be added subsequent to any cooking process.

Also, the fungicidally active compounds of the invention may be used as fungicidal additive to growth media for various microorganisms such as *E. coli, Pseudomonas aeroginosa, Serpula lacrymans* and *Cladosporium* sp.

DESCRIPTION OF THE STRAIN

Colonies: grey, cottony, sometimes zonate.

Conidiophores: Single to aggregated, simple, straight to flexuous, geniculate above.

Conidia: acropleurogenous, 2–4 septate when mature, smooth, but becoming verrucose on the large central cell, mostly curved, concolourous or with central cell more pigmented than the other cells, mostly 20–39 μm long and 11–14 μm thick in the broadest part.

CMI CC 337159 is 4 septate like *C. verruciformis*, but differs from it in the size of the conidia. The conidia of *C. verruciformis* are 16–26 μm×8–12 μm in size. CMI CC 337159 is a new species in the genus Curvularia. It belongs to the class Deuteromycetes, sub-class Hyphomycetidae and family Dematiaceae.

CULTIVATION OF THE STRAIN

The fungus may be grown on agar slants containing the following ingredients in grams/liter:

| | |
|---|---|
| yeast extract | 4.0 |
| potassium dihydrogen phosphate | 1.0 |
| magnesium sulphate heptahydrate | 0.1 |
| glucose | 15 |
| Bacto (Difco Laboratories, Detroit, USA) agar | 20 |

This substrate is autoclaved at 121° C. for 20 or 40 minutes and will, hereinafter, be referred to as YPG agar. Slants contain 12 ml YPG agar and after inoculation they are incubated at 20°–25° C. for 7 days or longer.

FUNGICIDE PRODUCTION

A substrate for shake flasks was prepared using demineralized water with the following ingredients in grams per liter:

| | |
|---|---|
| yeast extract | 4.0 |
| potassium dihydrogen phosphate | 1.0 |
| magnesium sulphate heptahydrate | 0.1 |
| glucose | 15 |
| pluronic ® L61 (BASF, Federal Republic of Germany) | 0.1 |

Sterilization took place at 121° C. for 20 minutes. A 500 ml Erlenmeyer flask with 100 ml of substrate was inoculated with about $10^6$ spores from a YPG agar slant previously inoculated with CMI CC 337159. The flasks were shaken at 230 rpm at 25° C. for 3–7 days whereafter the fermentation broth was centrifuged. The supernatant containing the fungicide was thereby separated from the mycelium. Both the mycelium and the supernatant were analyzed for fungicidal activity.

The fungicide can also be produced in surface cultures in accordance with well known procedures.

The fermentation can also be carried out in media containing other sources of carbon and nitrogen assimilable by the micro-organism and generally low levels of inorganic salts. In addition, the media may be supplemented with trace metals, although if complex sources of carbon and nitrogen are employed, they are usually present in the complex sources.

EXTRACTION OF THE COMPOUND

Culture broth was drum filtered with High Flow Supercel® as precoat. To the filtrate was added 20 g/l XAD-8, and the mixture was stirred for 16 hours at 5° C.

The resin XAD-8, was then filtered off, and rinsed with 10 bed volumes 25% v/v ethanol with stirring for 30 minutes. The activity was first eluted with 2×3 volumes of 60% ethanol in 10 mM phosphate pH 7.0, and stirring for 60 minutes. The rest of the activity was eluted with 2×3 vol 80% v/v ethanol in 10 mM phosphate pH 7.0 and stirring for 60 minutes. The eluates were combined and concentrated to ⅕vol by vacuum evaporation at temperatures <40° C.

3.6 liters of concentrated eluates were further concentrated to 750 ml. The concentrate was then centrifuged and the precipitate was discarded. The supernatant was extracted twice with 765 ml ethyl acetate. The combined ethyl acetate phases were frozen to remove water.

The water free extract was concentrated by vacuum evaporation to 20 ml and then added to 120 ml acetonitrile. Further concentration was done by vacuum evaporation to 25 ml, which was added to 70 ml deionized water and 70 ml ethanol, and vacuum evaporated until slightly cloudy. The solution was then placed in a refrigerator for crystallization. After 4 days the crystals were washed with deionized water and freeze dried.

Thereby 1 g of crystals was obtained.

For simplicity the compound of formula IV hereinafter will be designated BK202.

TEMPERATURE AND pH STABILITY

Procedure: The compound BK202 was solubilized in buffer at the pHs indicated in FIG. 1, and then placed at 25°–55° C. for 16 hours. The buffers used were phosphate-citrate (T. C. McIlvaine, J. Biol. Chem. 49,183(1921), in the pH range 2.5–7 and from pH 7–9.5 is used TRIS 0.05M. After 16 hours, the samples were filtered on a membrane filter 0.45 μm, and then analyzed by the HPLC method.

FIG. 1 shows the relationship between residual activity and pH for a number of temperatures. From the figure it is seen that the compound of formula IV of the invention exhibit stability optimum about pH 7, where the stability seems independent of temperature, whereas stability at pH values above 8 decreases rapidly. At pH values below 7 the stability decreases slowly except for the temperature 25° C., where the decrease seems to be rapid. However, this may reside in experimental error.

| Analysis — HPLC method | |
|---|---|
| Column: | Spherisorb Hexyl 5 μm, 140 mm × 4.6 mm |
| Flow: | 1.5 ml/min |
| Detection: | 220 nm and 210 nm |
| Eluent: | 55% Acetonitrile + 0.1% Trifluor acetic Acid |
| Sample: | 10 μl |
| Retention time: | ca. 6.3 minutes |

PHYSICAL AND CHEMICAL PROPERTIES

Crystallization of the material, obtained by the isolation procedure previously described, from aqueous ethanol gives white crystals with the physico-chemical properties described below (oven dried at 80° C. for two hours and stored overnight in a vacuum desiccator over anhydrous silica).

| 1. Physical properties | |
|---|---|
| Nature | colourless crystals |
| MP | 194–195° C. |
| $[\alpha]_D^{21}$ (C = 0.4, MeOH) | 205° |
| Analysis | |
| Found | C: 59.44 |
| | H: 8.14 |
| | N: 10.89 |
| Calculated for $C_{56}H_{89}N_9O_{14} \cdot H_2O$ | C: 59.50 |
| | H: 8.11 |
| | N: 11.15 |

Crystallization of the material from methanol yields anhydrous white crystals with the physico-chemical properties described below (oven dried at 80° C. for two hours and stored overnight in a vacuum desiccator over anhydrous silica).

| 1. Physical properties | |
|---|---|
| Nature | colourless crystals |
| MP | 210–212° C. |
| $[\alpha]_D^{21}$ (C = 0.4, MeOH) | –227° |
| Analysis | |
| Found | C: 60.11 |
| | H: 8.00 |
| | N: 11.28 |
| Calculated for $C_{56}H_{89}N_9O_{14}$ | C: 60.48 |
| | H: 8.06 |
| | N: 11.33 |
| Mass spectrum (FAB) | MH+ 1112.6 |

2. Chemical properties

Total acid hydrolysis (6N HCl, 18–24 h, 110° C.) yielded the following α-amino and hydroxy acids (determined by Gas Chromatography/Mass Spectral-analysis of triflouroacetyl-n-butylester derivatives, numbers in parenthesis indicate the number of occurrences of each amino acid).

| Lactate (1) | $C_3H_4O_2$ |
|---|---|
| Glycine (1) | $C_2H_3NO$ |
| Valine (1) | $C_5H_9NO$ |
| N—Me-Valine (3) | $C_6H_{11}NO$ |
| N—Me-Isoleucine (1) | $C_7H_{13}NO$ |
| pipecolic acid (1) | $C_6H_9NO$ |
| N—Me-Aspartic acid (1) | $C_5H_7NO_3$ |
| O—Me-Tyrosine (1) | $C_{10}H_{11}NO_2$ |
| | $C_{56}H_{89}N_9O_{14}$ |

The compound BK202 of the invention is negative to ninhydrin-test, contains no -XH function that can be acetylated (Acetic anhydride/pyridine, 24 hours, room temperature) and has one free carboxyl group, which can be esterified by treatment with diazomethane to the corresponding monomethylester BK202-Me (Cf-PDMS, MH+ 1126.5).

The compound BK202 of the invention contains a lactone linkage (IR 1736 cm$^{-1}$) which can be opened by mild alkaline hydrolysis (0.1N NaOH; 0.5 h, room temperature) to yield a ring opened derivative BK202-OH. By treatment with diazomethane BK202-OH can be turned into the corresponding dimethylester BK202Me$_2$ (Cf-PDMS, MH+ 1158.4).

SPECTRAL DATA

BK202

$^1$H-NMR: Due to the complexity of the spectra induced by the co-existence of more conformers only a partial assignment shown in Table I has yet been made.

TABLE I

Partial assignment of the $^1$H-NMR spectrum (FIG. 2) Chemical shift values for major conformer relative to TMS (multiplicity (d = doublet, t = triplet, dd = double doublet, q = quartet, m = multiplet, br = broad), J-values in Hz)

| Residue | NH | α-H | β-H | γ-H | others |
|---|---|---|---|---|---|
| O—MeTyr | 7.50 (d, 10) | 5.20 (m) | 3.25 (2H, m) | — | 7.00(2H, d, 8) 6.70(2H, d, 8) |
| Val | 7.00 (d, 10) | 4.55 (t, 10) | 2.10 (m) | 0.80, 0.89 (2 Me, d, 7) | — |
| Gly | 7.08 (br) | 4.02 (dd, 6/18) | — | — | — |
| NMe—Val | — | 5.19 (d, 11) | 2.37 (m) | 0.88, 0.98 (2 Me, d, 7) | — |
| NMe—Val | — | 4.31 (d, 10) | 2.43 (m) | 0.89, 1.06 (2 Me, d, 7) | — |
| NMe—Val | — | 4.74 (d, 10) | 2.13 (m) | 0.68, ? (Me, d, 7) | — |
| Lac | — | 5.47 (q, 7) | 1.40 (Me, d, 7) | — | — |

Figure 2:
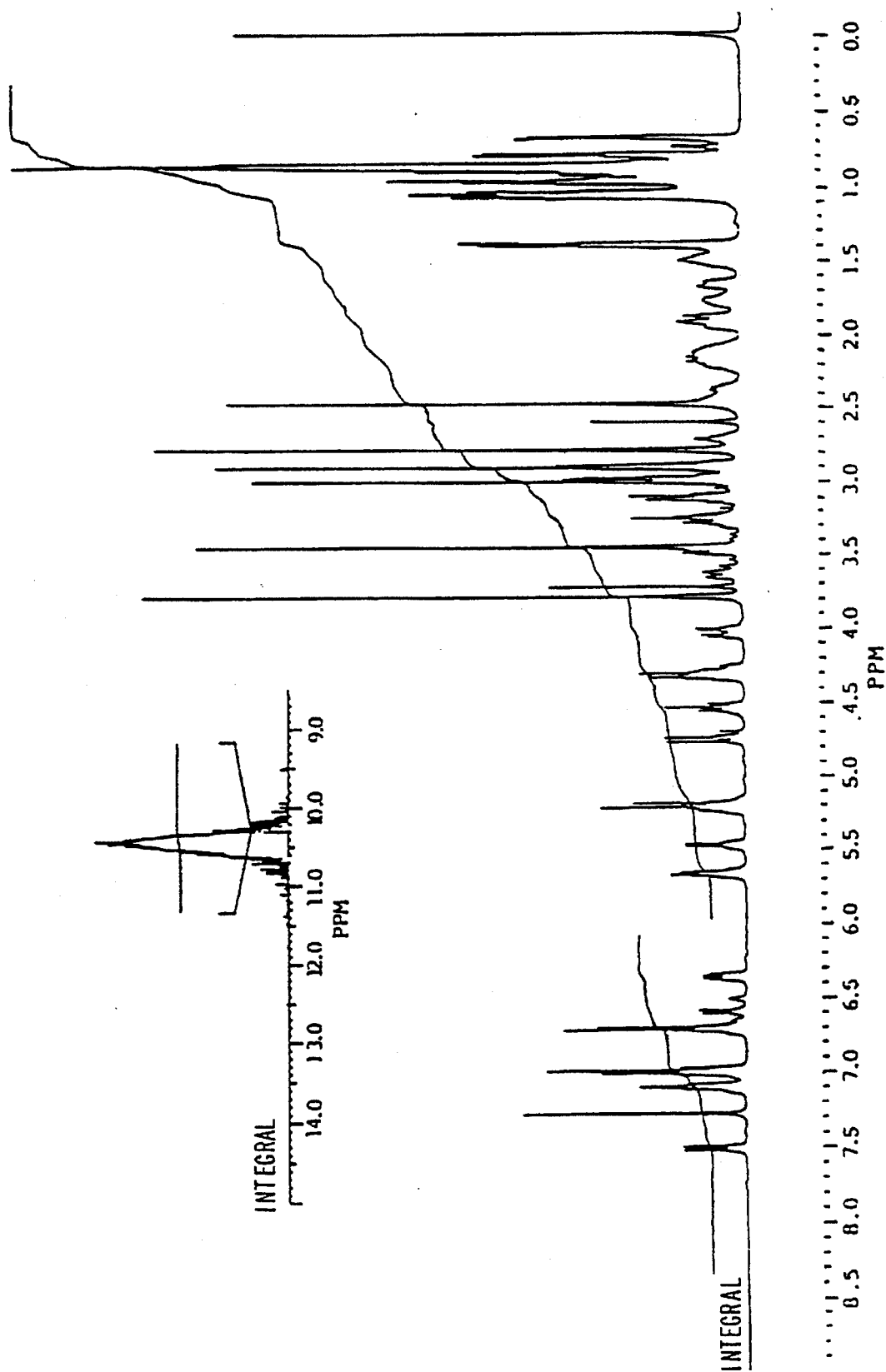
FIGS. 2, 3, and 4 show 400 MHz $^1$H-NMR spectra of the isolated compound of the invention in $CDCl_3$, $DMSO-d_6$, and $CD_3OD$, respectively.
Figure 3:
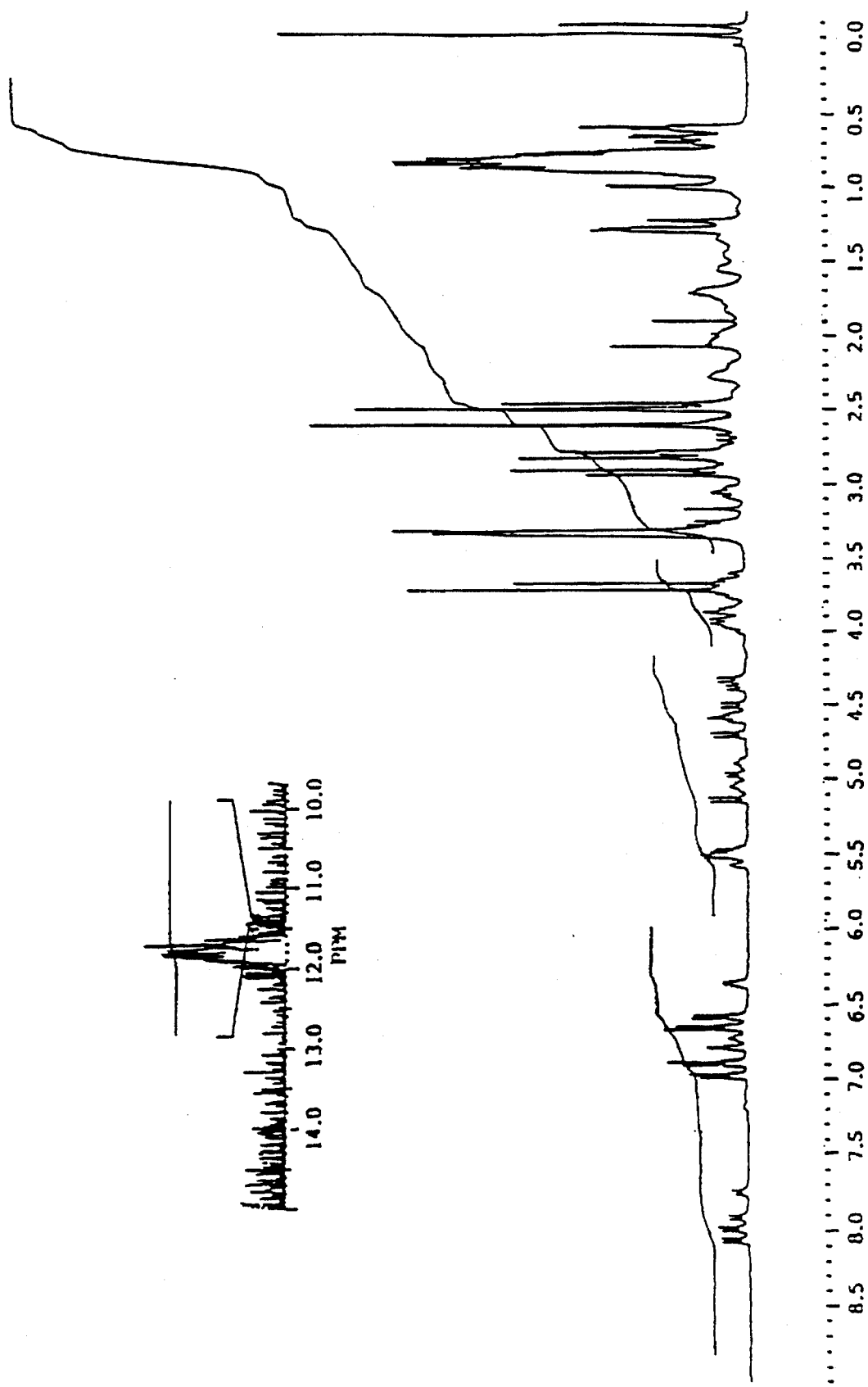
Figure 4:
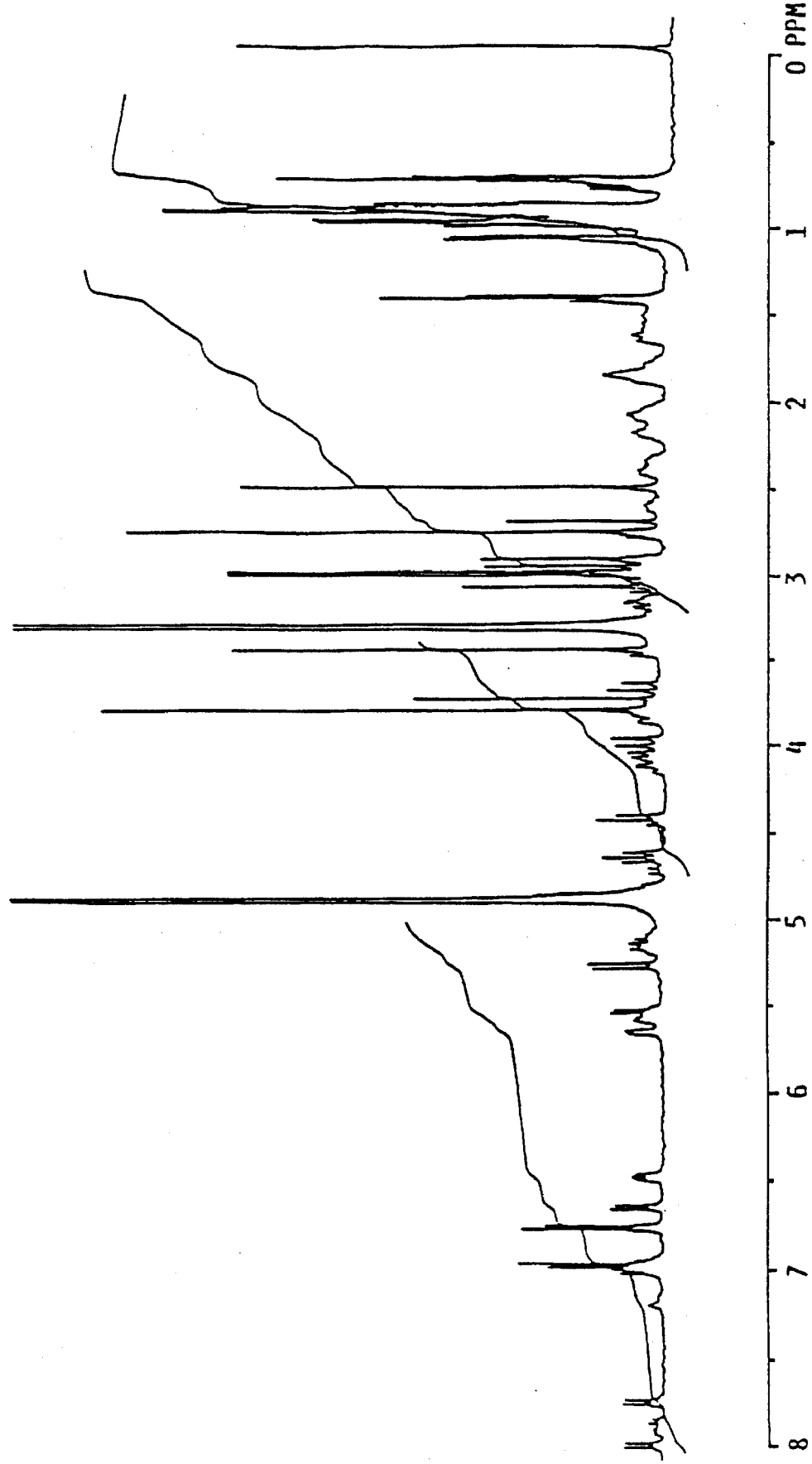
Figure 5:
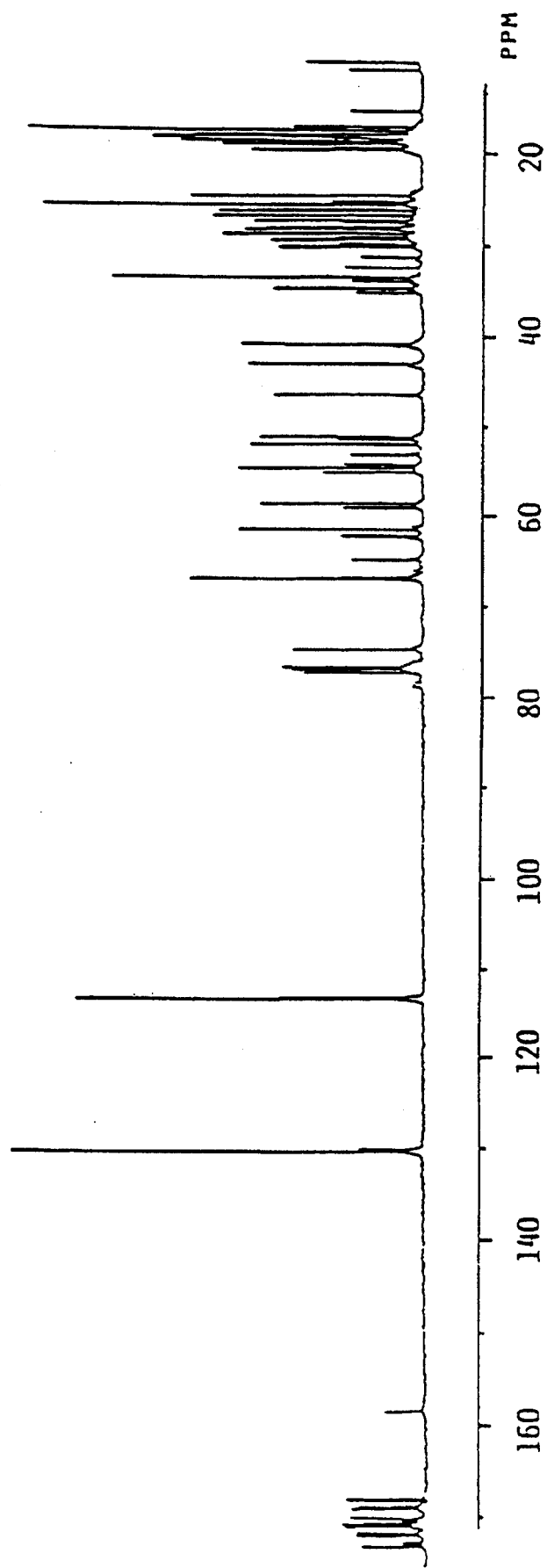
FIG. 5 shows a 100.6 MHz $^{13}$C-NMR spectrum of the isolated compound of the invention in $CDCl_3$.
Figure 6:
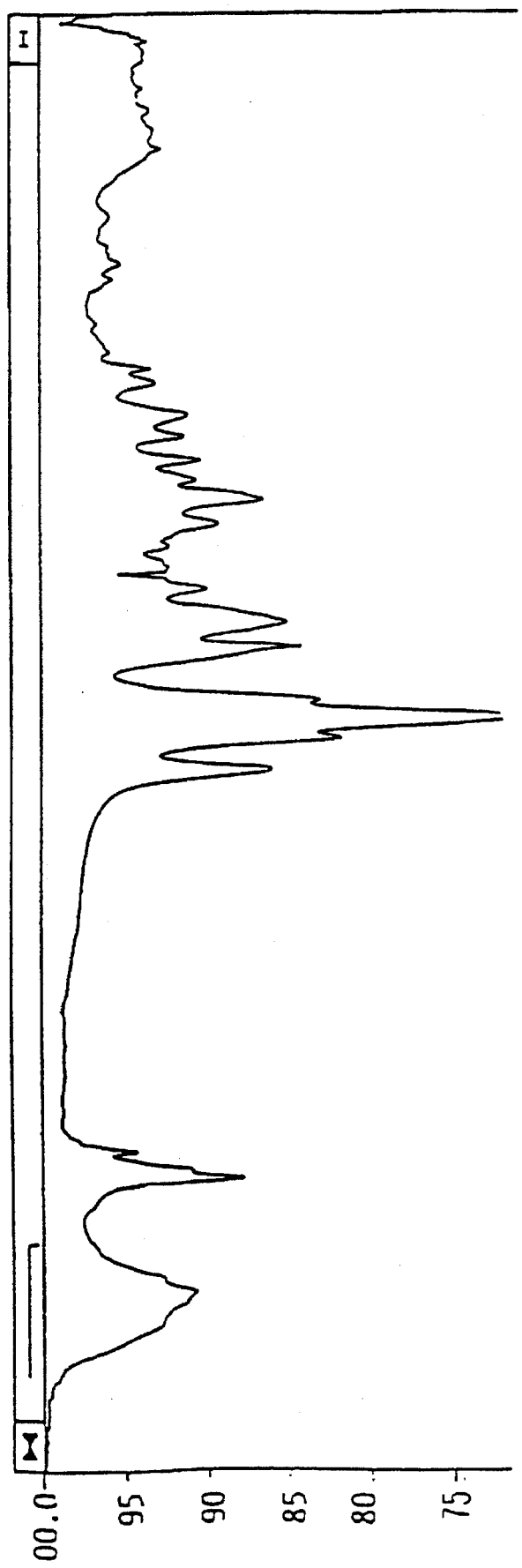
FIG. 6 shows an infra-red (IR) spectrum of the isolated compound of the invention in KBr.

The $^1$H-NMR-data are presented as raw spectra in FIGS. 2 to 4. (FIG. 2, FIG. 3 and FIG. 4:400 MHz spectra in CDCl$_3$, DMSO-d$_6$ and CD$_3$OD, respectively).
$^{13}$C-NMR: 100.6 MHz in CDCl$_3$ (FIG. 5)
IR: KBr (FIG. 6)

Derivatives of BK202

Figure 7:
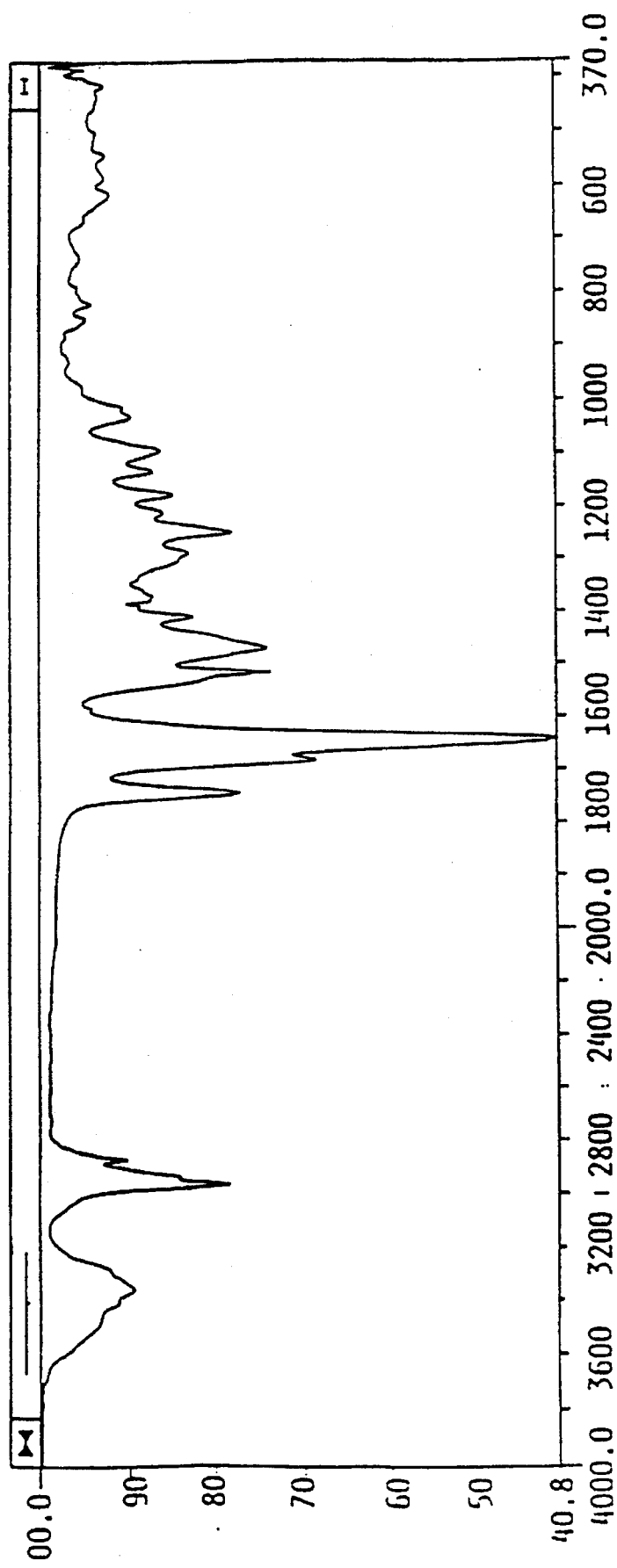
FIG. 7 shows an IR spectrum of a methylated derivative in KBr.

BK202-Me
IR: KBr (FIG. 7)

BIOASSAY

10$^6$ spores of *Botrytis cinerea* were added to 50 ml dilute salts comprising:

| ammonium hydrogen phosphate | 66 mg |
|---|---|
| potassium dihydrogen phosphate | 68 — |
| dipotassium hydrogen phosphate | 87 — |
| calcium chloride-2-hydrate | 7.4 — |
| magnesium chloride-6-hydrate | 10 — |

Prior to the inoculation the salt solution was made up to 1 liter with distilled water and sterilized at 121° C. for 20 minutes.

This was mixed with 50 ml YPG agar at a temperature which favoured the viability of Botrytis spores in the temperature range from 30° C. to about 45° C. where the agar is kept fluid without any harm to the spores. 12 ml of this mixture were poured into 9 cm petri dishes and allowed to solidify. 1–5 holes of 4 mm diameter were punched in the agar and 15 μl culture broth was put in each hole.

The petri dishes were incubated at 20°–25° C. for 2 days. The presence of a fungicide will reveal itself as a clear non-growth zone around the holes—the larger the zone the stronger the fungicide. The supernatant of CMI CC 337159 under the conditions described above, produced a rather diffuse zone with a diameter of 40 mm. Under a stereo microscope, it can be seen that the fungus is present but normal growth has been prevented. Under a light microscope the mycelium appears as large vesicles, suggesting a particular type of mode of action.

MAMMALIAN PATHOLOGY

Culture broth containing the fungicide, viable spores and mycelium showed no effect on mice, intraperitoneallly applied at the rate of 20 ml per kg body weight. The broth contained approximately $4.5 \times 10^7$ viable counts/ml.

TOXICOLOGY

The toxicity of BK 202 was investigated in the following tests using the compound of formula IV in crystaline form:

Acute oral and intravenous toxicity in mice, and

Ames spot tests and in vitro testing of dermal irritation (Skintex®).

The animals were given the active ingredient in dosages up to 1600 mg/kg orally in a suspension, and up to 13 mg/kg in a solution applied intraveneously to the tail.

Based on these tests the $IC_{50}$ values for BK 202 were estimated as:

ATP>10 µg/ml;

Chemiluminescent>10 µg/ml

Consequently it can be concluded that BK 202 shows no indication of toxicity in the tests performed, and also BK 202 scored the lowest possible irritation in the Skintex® test.

FUNGICIDAL ACTIVITY

Experiments were carried out to determine the potency of the compound of formula IV towards various fungi. The active ingredient was dissolved in 60% ethanol and added to cooled potato dextrose agar to give final concentrations of 25, 5, 1, 0.2, 0.04 and 0.0016 µg a.i. per ml agar, respectively. Control dishes contained no active ingredient.

10 ml Agar was poured into 9 cm petri dishes and each concentration was inoculated with actively growing mycelium of the fungal isolates tested for. The dishes were incubated at the optimum temperature for growth of the isolates for 3 to 6 days after which time the growth was measured in mm and compared to the controls.

The test isolates covered a broad range of fungi within the Oomycetes, the Ascomycetes, the Basidiomycetes, the Deuteromycetes, and the Zygomycetes.

It was found that BK 202 was most active against fungi belonging to the Ascomycetous and the Deuteromycetous species. It was found to be particularly potent towards:

Class Ascomycetes, genus Venturia, e.g. *V. inequalis* genus Sclerotinia, e.g. *S. sclerotiorum* genus Monilinia, e.g. *M. fructigena,* form-genus Aspergillus, e.g. *A. fumigatus* form-genus Penicillium, e.g. *P. digitatum*

Class Deuteromycetes, genus Botrytis, e.g. *B. cinerea* genus Ascochyta, e.g. *A. pisi* genus Pyrenophora, e.g. *P. teres* genus Cercospora, e.g. *C. beticola*(weaker)

genus Phoma, e.g. *P. sorghina*(weaker)

genus Alternaria, e.g. *A. alternata*(weaker)

genus Fusarium, e.g. *F. lycopersici*(weaker)

For the above fungi the inhibition was very strong in as low concentrations as 0.0016 µg/ml, except for *C. beticola, P. sorghina, A. alternata,* and *F. lycopersici,* where a weaker inhibition was found.

Only weak activity was found against Zygomycetous species, and practically no activity was found towards Oomycetous and Basidiomycetous species.

BIOLOGICAL ACTIVITY ON PLANTS

At the concentrations used in the following examples no phytotoxic activity has been observed.

EXAMPLES

EXAMPLE 1

Activity against *Botrytis cinerea* on tomato plants

Tomato plants (variety "First in Field", 3 weeks old) were treated with a liquid suspension containing 0.035 mg active ingredient per ml. The plants were kept 24 hours in a green house to dry before they were inoculated with a spore suspension containing $10^5$ *Botrytis cinerea* spores per ml in 25% grapefruit juice. The plants were then incubated for 6 days (16 hours light (1000 lux) and 8 hours dark at 15° C. to 20° C.) in clear polyethylene bags to raise the relative humidity to 95–100%. No attack from the fungus was observed. Control plants that were treated as above except for the application of the active ingredient in suspension were all overgrown with *Botrytis cinerea*.

EXAMPLE 2

Activity against *Botrytis cinerea* on apples (Golden Delicious)

Artificially injured apples were sprayed with a suspension containing 9.81 µg active ingredient per ml. On the following day the treated fruits were inoculated with a spore suspension of the fungus containing $1 \times 10^5$/ml, and incubated for a week at high air humidity and 18°–20° C. At the evaluation the infected places of injury were counted and from that the fungicidal effect of the test substance evaluated. The active compound prevented the growth of fungus completely. The untreated fruits were 100% infected with *Botrytis cinerea*.

EXAMPLE 3

Activity against *Botrytis cinerea* on strawberries (Senga-Sengana)

Field trial performed in Funen, Denmark, in accordance with the EPPO guidelines (Guideline for the Biological Evaluation of Fungicides. *Botrytis cinerea* on Strawberries).

The plot size was 20 m² and three replicates were used. The active compound was used in a test formulation containing approximately 10% active ingredient (a.i.). Three concentrations of active compound were applied: 100, 300, and 900 g a.i./ha. The spraying volume was 1200 l/ha.

The strawberries were sprayed at the following growth stages: $T_1$, onset of flowering; $T_2$, 10% flowering; $T_3$, 50% flowering; and $T_4$, 80% flowering.

The commercial fungicide ROVRAL® was used as standard reference.

The assessment was performed by counting and weighing healthy and infected strawberries, respectively.

Figure 8:
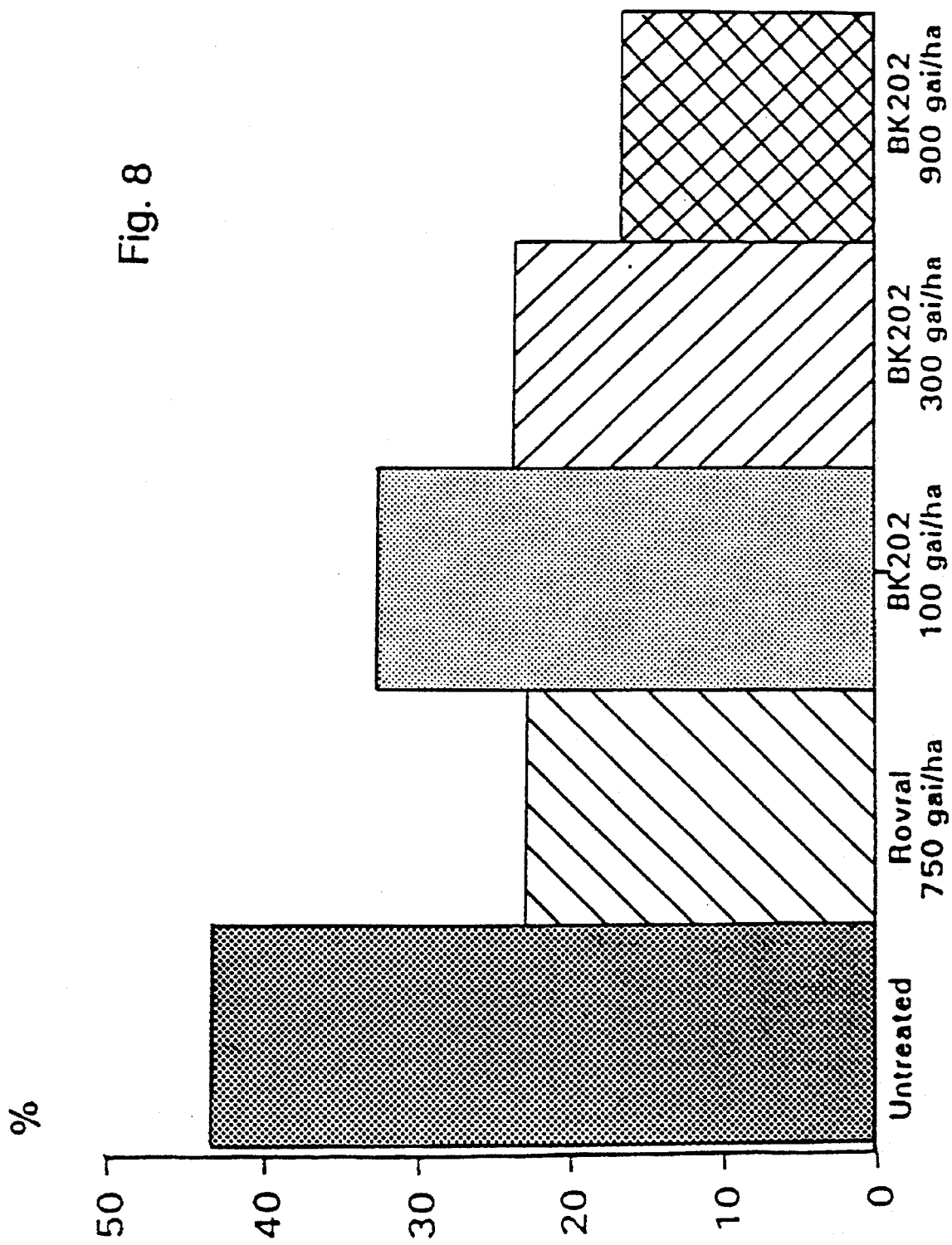

The results are shown in FIG. 8, where the degree of infection is indicated for each of the tests. From FIG. 8 it is seen that BK 202 exhibited a superior fungicidal effect compared to ROVRAL®.

EXAMPLE 4

Activity against *Botrytis cinerea* on grapes(Ugni Blanc)

Field trial performed in Bordeaux, France, in accordance with CEB Method No. 37.

A plot consisted of 15 plants in one row and six replicates were used. The active compound was used in a test formulation containing approximately 10% active ingredient (a.i.). Three concentrations of active compound were applied: 100, 300, and 900 g a.i./ha. The water volume was 300 l/ha.

The grapes were sprayed at the following growth stages: $T_1$, end of formation of bunches of grapes; $T_2$, beginning of ripening of grapes; and $T_3$, 3 to 4 weeks before harvest.

The commercial fungicides RONILAN® and BASULTRA® were used as standard references The assessment was performed by estimating the intensity and frequency of the *Botrytis cinerea* attack after the appearance of the disease.

Figure 9:
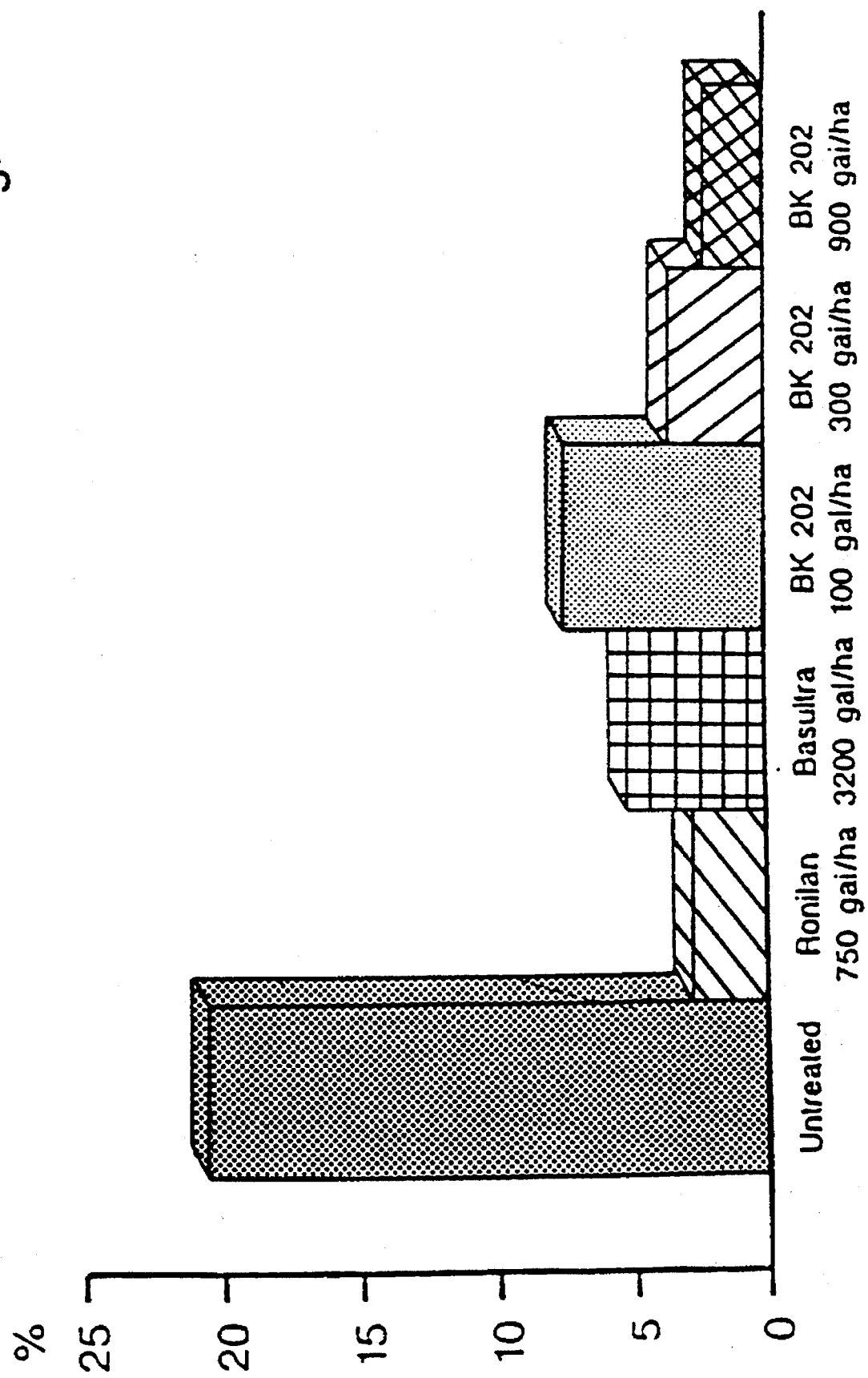

The results are shown in FIG. 9, where the intensity of infection is indicated (defined as % attacked grapes in 100 bunches) for each of the tests. From FIG. 9 it is seen that BK 202 exhibited a superior fungicidal effect compared to both RONILAN® and BASULTRA®.

EXAMPLE 5

Activity against *Botrytis cinerea* on tomatoes (Matador)

Green house trial performed in Lyngby, Denmark.

A plot consisted of 7 plants (approximately 12 weeks old, 1 m high) and three replicates were used. The plants were kept in a plastic "tent" to maintain a high humidity. Before spraying the plants 20 leaves per plant were mechanically injured to improve the attack of *Botrytis cinerea*. The active compound was used in a test formulation containing approximately 10% active ingredient (a.i.). Three concentrations of active compound were applied: 0.01%, 0.03%, and 0.09% a.i. The water volume was 770 ml/plot.

The tomatoes were sprayed just after wounding the leaves. 24 hours after fungicide treatment an artificial inoculation was done by spraying spores of *B. cinerea* suspended in 30% orange juice on the plants.

The commercial fungicide RONILAN® was used as standard reference.

The assessment was performed by counting the number of attacks on leaves, stalks, fruits, and flower buds.

The results are shown in FIG. 10, where the degree of infection is indicated for each of the tests. From FIG. 10 it is seen that BK 202 at all the tested concentrations exhibited a superior fungicidal effect compared to RONILAN®.

EXAMPLE 6

Activity against fungicide resistant *Botrytis cinerea* isolates

One isolate resistant to BENLATE® (isolate A), and one isolite resistant to BENLATE®,ROVRAL® and SUMISCLEX® (isolate B) were isolated from plants which had been sprayed with the above mentioned pesticides. The effect of BK 202 on these isolates was determined in an in vitro assay and compared with the three commercial pesticides. The fungicides were added to agar and dispensed in petri dishes at different concentrations and were inoculated with a sensitive (normal(isolate C)) and the two resistant strains. After 3 days at a temperature of 25 C. growth was measured in mm.

The results are shown in Table II below.

TABLE II

| Pesticide | concentration | Isolate A | Isolate B | Isolate C |
|---|---|---|---|---|
| BK 202 | 10 | 0 | 0 | 0 |
|  | 2 | 0 | 0 | 0 |
|  | 0.125 | 0 | 0 | 0 |
| ROVRAL ® | 10 | 0 | 13 | 0 |
|  | 2 | 0 | 46 | 0 |
| BENLATE ® | 10 | 50 | 50 | 0 |
|  | 2 | 65 | 62 | 0 |
| SUMISCLEX ® | 10 | 0 | 35 | 0 |
|  | 2 | 0 | 46 | 0 |
| Control | — | 76 | 80 | 74 |

EXAMPLE 7

Activity against *Monilinia fructigena* on apples (Golden Delicious)

Apples were surface sterilized, each punctured 5 times with a nail 2.1 mm in diameter, dipped in suspensions containing 0, 0.5, 5, 50, and 500 mg a.i. per l. The active ingredient was (i) BK 202, (ii) benomyl(BENLATE®), (iii) iprodione(ROVRAL®). Four apples were punctured and treated with each concentration of the three pesticides giving a total of 20 wounds per concentration. The fruits were placed in plastic containers in rows with the wounds facing upwards. After 24 hours, the wounded areas were sprayed with a suspension of *Monilinia fructigena* containing $1 \times 10^5$ spores per ml. The containers were then covered with polyethylene bags and kept at room temperature (approximately 22° C.).

After 5 days the effects were assessed by counting the number of infected wounds (maximum 20 infected wounds per treatment).

The results are indicated in Table III.

TABLE III

| Concentration | BK 202 | BENLATE ® | ROVRAL ® |
|---|---|---|---|
| 0 mg ai/l | 20 | 20 | 20 |
| 0.5 mg ai/l | 18 | 18 | 20 |
| 5.0 mg ai/l | 14 | 19 | 19 |
| 50 mg ai/l | 7 | 12 | 15 |
| 500 mg ai/l | 1 | 3 | 4 |

From Table III it can be seen that the activity of BK 202 towards *M. fructigena* is superior in comparison to the two commercial fungicides tested.

Examples of further crops considered protectable against fungal attacks are: pears, plums, peaches, cherries, raspberries, beans, peas, soya, oil cultures like rape, mustard, olives, sunflowers etc., cereals, cucumbers, melons, citrus fruits like oranges, lemons, mandarin oranges etc., spinach, lettuce, potato, pepper, avocado, aubergine, banana, composites like gerbera and other ornamental plants etc.

We claim:

1. Compounds of formula III (III)

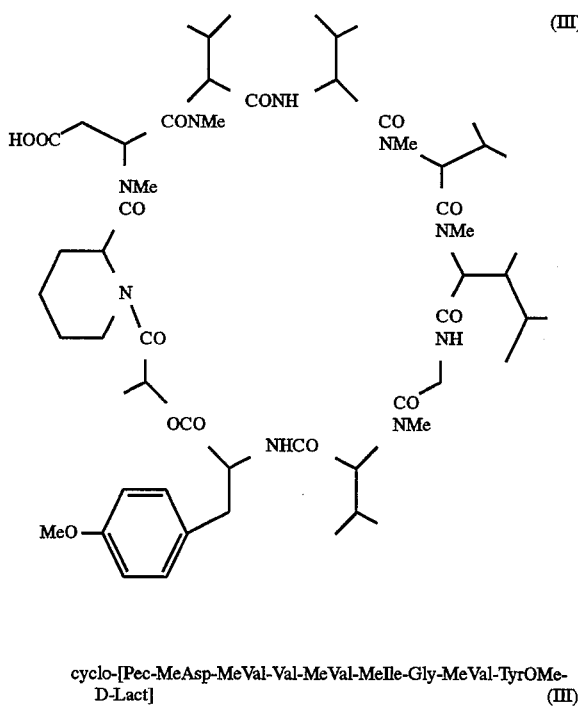

cyclo-[Pec-MeAsp-MeVal-Val-MeVal-MeIle-Gly-MeVal-TyrOMe-D-Lact] (III)

wherein each amino acid residue and the lactate residue independently may occur in L- or D-form, and derivatives thereof.

2. A process for the production of compounds claim 1 by a) cultivation on suitable nutrient media under suitable conditions of a species belonging to the genus Curvularia, b) subsequent recovery of the active component from the biomass and the fermentation medium, and c) optionally modifying the active compound to obtain a desired compound.

3. The process of claim 2, wherein the active compound has the formula III, and is obtained directly in step (b).

4. The compound of claim 1 in which all the amino acid residues are in the L-form and the lactate residue is in the D-form.

5. A method of combating fungi at a locus infested with fungi comprising applying to said locus the compound of claim 1.

6. A method of preventing infestation of fungi at a locus comprising applying to said locus the compound of claim 4 in an amount effective to combat the fungi.

7. The method according to claim 4 in which the locus is in a plant, on timber, cosmetics, in feed, in food, in growth media and in paint.

8. The method according to claim 4 in which the fungi belongs to the class Ascomycetes or Deuteromycetes.

9. The method according to claim 4 in which the fungi belongs to the genera selected from the group consisting of Venturia, Sclerotinia, Monilinia, Aspergillus, Penicillium, Botrytis, Ascochyta, Pyrenophora, Cercopora, and Phoma.

10. The method according to claim 4 in which the fungi belongs to the species *Botrytis cinerea.*

* * * * *